United States Patent
Naya

(10) Patent No.: US 7,027,159 B2
(45) Date of Patent: Apr. 11, 2006

(54) SENSOR UTILIZING EVANESCENT WAVE

(75) Inventor: Masayuki Naya, Kaisei-machi (JP)

(73) Assignee: Fuji Photo Film Co., Ltd., Kanagawa-ken (JP)

(*) Notice: Subject to any disclaimer, the term of this patent is extended or adjusted under 35 U.S.C. 154(b) by 8 days.

(21) Appl. No.: 10/328,165

(22) Filed: Dec. 26, 2002

(65) Prior Publication Data
US 2003/0156292 A1 Aug. 21, 2003

(30) Foreign Application Priority Data
Dec. 25, 2001 (JP) ............................. 2001-390942

(51) Int. Cl.
*G01N 21/55* (2006.01)

(52) U.S. Cl. .................................................. 356/445
(58) Field of Classification Search ......... 356/445–448
See application file for complete search history.

(56) References Cited

U.S. PATENT DOCUMENTS

| | | | | |
|---|---|---|---|---|
| 4,997,278 | A * | 3/1991 | Finlan et al. ................ | 356/128 |
| 5,313,264 | A * | 5/1994 | Ivarsson et al. .............. | 356/73 |
| 5,485,277 | A * | 1/1996 | Foster ......................... | 356/445 |
| 5,492,840 | A | 2/1996 | Malmqvist et al. | |
| 5,991,048 | A * | 11/1999 | Karlson et al. .............. | 356/445 |
| 6,628,376 | B1 * | 9/2003 | Nikitin et al. ............... | 356/38 |
| 2001/0040680 | A1 | 11/2001 | Kubo et al. | |
| 2002/0171841 | A1 * | 11/2002 | Elkind et al. ............... | 356/445 |

FOREIGN PATENT DOCUMENTS

| | | |
|---|---|---|
| EP | 0 863 395 A2 | 9/1998 |
| EP | 1 219 952 A1 | 7/2002 |
| EP | 1 251 345 A1 | 10/2002 |
| JP | 6-167443 A | 6/1994 |
| JP | 11326194 | 11/1999 |

OTHER PUBLICATIONS

Takayuki Okamoto/"Spectral Research", /Surface Refracto-Sensor Using Evanescent Waves: Principles and Instrumentations/ (Spectrum Researches, vol. 47, No. 1) (Optical Engineering Laboratory, The Institute of Physical and Chemical Research (RIKEN) Dec. 8, 1997.

J.D. Richards, et al. /Surface-Plasmon Excitation Using a Polarization-Preserving Optical Fiber and an Index-Matching Fluid Optical Cell/ Jun. 1, 1993/ vol. 32, No. 16/Applied Optics.

* cited by examiner

*Primary Examiner*—Michael P. Stafira
(74) *Attorney, Agent, or Firm*—Sughrue Mion, PLLC

(57) ABSTRACT

A sensor utilizing an evanescent wave and comprising a light source for emitting a light beam and a measuring chip formed into the shape of a well. The measuring chip has a dielectric block and a thin film layer formed on one surface of the dielectric block. The sensor also includes an optical system for making the light beam enter the dielectric block at angles of incidence so that a total internal reflection condition is satisfied at an interface between the dielectric block and the thin film layer. The sensor further includes a sample supply-discharge unit which is detachably installed within the measuring chip. The sample supply-discharge unit is used for continuously supplying the sample onto the surface of the thin film layer and continuously discharging the supplied sample from the surface of the thin film layer.

19 Claims, 7 Drawing Sheets

SENSOR UTILIZING EVANESCENT WAVE

BACKGROUND OF THE INVENTION

1. Field of the Invention

The present invention relates to a sensor, utilizing an evanescent wave, which analyzes a sample by causing a light beam to reflect at the interface between a thin film layer in contact with the sample and a dielectric block to generate an evanescent wave and then measuring a change in the intensity of the totally reflected light beam due to the evanescent wave.

2. Description of the Related Art

A surface plasmon resonance sensor is known as one utilizing an evanescent wave. If free electrons vibrate collectively in a metal, a compression wave called a plasma wave will be generated. The compression wave, generated in the metal surface and quantized, is called a surface plasmon. The surface plasmon resonance sensor is used to analyze the properties of a sample by taking advantage of a phenomenon that the surface plasmon is excited by a light wave. Various types of sensors have been proposed. Among such sensors, one employing the "Kretschmann configuration" is particularly well known (e.g., see Japanese Unexamined Patent Publication No. 6 (1994)-167443).

The surface plasmon resonance sensor employing the aforementioned "Kretschmann configuration" is constructed basically of (1) a dielectric block formed into the shape of a prism; (2) a metal film, formed on one surface of the dielectric block, for placing a sample thereon; (3) a light source for emitting a light beam; (4) an optical system for making the light beam enter the dielectric block at various angles of incidence so that a condition for total internal reflection is satisfied at the interface between the dielectric block and the metal film; (5) photodetection means for detecting the intensity of the light beam totally reflected at the interface; and (6) measurement means for measuring the state of surface plasmon resonance (SPR) on the basis of the result of detection obtained by the photodetection means.

In order to obtain various angles of incidence in the aforementioned manner, a relatively thin light beam may be caused to strike the above-described interface while changing the angle of incidence, or a relatively thick convergent or divergent light beam may be caused to strike the interface so that it has incident components at various angles. In the former, a light beam whose angle of reflection varies with a change in the angle of incidence can be detected by a small photodetector movable in synchronization with a change in the angle of reflection, or by an area sensor extending in the direction where the angle of reflection varies. In the latter, on the other hand, light beams reflected at various angles can be detected by an area sensor extending in a direction where the reflected light beams can be all received.

In the above-described surface plasmon resonance sensor, if a light beam strikes a metal film at a specific incidence angle $\theta_{sp}$ greater than a critical incidence angle at which total internal reflection (TIR) takes place, an evanescent wave having electric field distribution is generated in a sample in contact with the metal film. With the evanescent wave, the above-described surface plasmon is excited in the interface between the thin film layer and the liquid sample. When the wave number vector of the evanescent wave is equal to the wave number of the surface plasmon and therefore the wave numbers between the two are matched, the evanescent wave resonates with the surface plasmon and the light energy is transferred to the surface plasmon. As a result, the intensity of the light totally reflected at the interface between the dielectric block and the metal film drops sharply. This sharp intensity drop is generally detected as a dark line by the above-described photodetection means.

Note that the aforementioned resonance occurs only when the incident light beam is p-polarized light. Therefore, it is necessary to make settings in advance so that the incident light beam can strike the aforementioned interface as p-polarized light.

If the wave number of the surface plasmon is found from a specific incidence angle $\theta_{sp}$ at which attenuated total reflection (ATR) takes place (the angle $\theta_{sp}$ will hereinafter be referred to as an attenuated total reflection angle $\theta_{sp}$) the dielectric constant of a sample to be analyzed can be calculated by the following Equation:

$$K_{sp}(\omega) = \frac{\omega}{c} \sqrt{\frac{\varepsilon_m(\omega)\varepsilon_s}{\varepsilon_m(\omega) + \varepsilon_s}}$$

where $K_{sp}$ represents the wave number of the surface plasmon, $\omega$ represents the angular frequency of the surface plasmon, c represents the speed of light in vacuum, and $\varepsilon_m$ and $\varepsilon_s$ represent the dielectric constants of the metal and the sample, respectively.

If the dielectric constant $\varepsilon_s$ of the sample is found, the concentration of a specific substance in the sample is found based on a predetermined calibration curve, etc. As a result, the dielectric constant of the sample, that is, the properties of the sample related to the refractive index, can be found by finding the attenuated total reflection angle $\theta_{sp}$.

In addition, a leaky mode sensor is known as a similar sensor making use of an evanescent wave (for example, see "Spectral Researches," Vol. 47, No.1 (1998), pp. 21 to 23 and pp. 26 to 27). This leaky mode sensor consists basically of (1) a dielectric block formed into the shape of a prism; (2) a cladding layer formed on one surface of the dielectric block; (3) an optical waveguide layer, formed on the cladding layer, for placing a sample thereon; (4) a light source for emitting a light beam; (5) an optical system for making the light beam enter the dielectric block at various angles of incidence so that a condition for total internal reflection is satisfied at the interface between the dielectric block and the cladding layer; (6) photodetection means for measuring the intensity of the light beam totally reflected at the interface; and (7) measurement means for measuring the excited state of a waveguide mode on the basis of the result of detection obtained by the photodetection means.

In the above-described leaky mode sensor, if a light beam strikes the cladding layer through the dielectric block at an incidence angle greater than a critical incidence angle at which total internal reflection (TIR) takes place, the light beam is transmitted through the cladding layer. Thereafter, in the optical waveguide layer formed on the cladding layer, only light with a specific wave number, incident at a specific incidence angle, propagates in a waveguide mode. If the waveguide mode is excited in this manner, most of the incident light is confined within the optical waveguide layer, and consequently, ATR occurs in which the intensity of light totally reflected at the aforementioned interface drops sharply. The wave number of the light propagating through the optical waveguide layer depends upon the refractive index of the sample on the optical waveguide layer. Therefore, the refractive index of the sample and the properties of the sample related to the refractive index can be analyzed by finding the attenuated total reflection angle $\theta_{sp}$ at which ATR occurs.

In the field of pharmaceutical research, the above-described surface plasmon resonance sensor and leaky mode sensor are sometimes used in a random screening method for detecting a specific substance that is coupled to a sensing substance. In this case, the sensing substance is fixed on the aforementioned thin film layer (which is the aforementioned metal film in the case of surface plasmon resonance sensors, or the cladding layer and optical waveguide layer in the case of leaky mode sensors). Then, a liquid sample containing various target substances is supplied onto the sensing substance. And each time a predetermined time elapses, the attenuated total reflection angle $\theta_{sp}$ is measured. If a target substance in the liquid sample is a substance that is coupled to the sensing substance, then the coupling will cause the refractive index of the sensing substance to vary with the lapse of time. Therefore, every time a predetermined time elapses, the attenuated total reflection angle $\theta_{sp}$ is measured. Based on the measured value, it is measured whether or not a change has occurred in the attenuated total reflection angle $\theta_{sp}$. Based on this result, it can be judged whether or not the target substance has been coupled to the sensing substance. That is, it can be judged whether or not the target substance is a specific substance that is coupled to the sensing substance. Examples of such a combination of a specific substance and a sensing substance are a combination of an antigen and an antibody, and a combination of an antibody and an antibody. A typical example of the measurement of such a combination is detection of the coupling between a human IgG (immunoglobulin G) antibody (which is a target substance) and a rabbit antihuman IgG antibody (which is a sensing substance) and a quantitative analysis thereof.

Note that in order to measure the coupled state between a target substance in a liquid sample and a sensing substance, the attenuated total reflection angle $\theta_{sp}$ itself does not always need to be detected. For example, a liquid sample with a target substance is added to a sensing substance. Then, a change in the attenuated total reflection angle $\theta_{sp}$ is measured. Based on the magnitude of the change, the coupled state between the target substance and the sensing substance can be measured.

In addition, the present inventors have proposed a sensor that is used to measure the above-described state of ATR by employing a measuring chip in the shape of a well which is easy to handle in making a measurement (e.g., Japanese Unexamined Patent Publication No. 2002-296172). In the case of a liquid sample, for example, a measurement can be made if only a small quantity of a liquid sample is supplied within the measuring chip. In addition, by employing a turntable capable of holding a plurality of measuring chips, a wide variety of samples can be measured in a short time.

In the sensor utilizing an evanescent wave, there are various methods of analyzing a sample by detecting the intensity of a light beam totally reflected at the aforementioned interface with photodetection means. For instance, a light beam is caused to strike the aforementioned interface at various angles of incidence so that a condition for total internal reflection (TIR) is satisfied at the interface. Then, the intensity of the light beam totally reflected at the interface is measured at each position corresponding to each incidence angle. Next, by detecting the position (attenuated total reflection angle $\theta_{sp}$) of a dark line produced due to attenuated total reflection (ATR), the state of ATR is measured. In this way, the properties of a sample held by the measuring chip of the sensor may be analyzed. In addition, a light beam with a plurality of wavelengths is caused to enter a measuring chip at angles of incidence so that a total internal reflection condition is satisfied at the interface. Then, the intensity of the light beam totally reflected at the interface is measured for each wavelength. Next, by measuring the degree of ATR for each wavelength, the properties of a sample held by the measuring chip may be analyzed (see D. V. Noort, K. Johansen, C. -F. Mandenius, Porous Gold in Surface Plasmon Resonance Measurement, EUROSENSORS XIII, 1999, pp. 585–588).

Furthermore, a light beam is caused to enter a measuring chip at angles of incidence so that a total internal reflection condition is satisfied at the aforementioned interface. Then, the light beam is split into two light beams before the light beam strikes the interface. One of the two light beams is caused to interfere with the other light beam totally reflected at the interface. Next, by measuring the intensity of the light beam after the interference, the properties of a sample held by the measuring chip may be analyzed (see P. I. Nikitin, A. N. Grigorenko, A. A. Beloglazov, M. V. Valeiko, A. I. Savchuk, O. A. Savchuk, Surface Plasmon Resonance Interferometry for Micro-Array Biosensing, EUROSENSORS XIII, 1999, pp. 235–238).

As a sensor that analyzes the properties of a sample by utilizing an evanescent wave, there is known a sensor which makes a measurement by continuously supplying a liquid sample onto a sensing substance fixed on a measuring chip in the shape of a flat plate, using a flow passage mechanism. In measuring the coupled state between a sensing substance and a specific substance, a new liquid sample is always supplied onto the measuring chip. Therefore, since the concentration of a target substance in the liquid sample is kept constant, the coupled state can be accurately measured. In addition, in the case where the coupled state between the sensing substance and the specific substance is measured, and the coupling between the two has been performed, the decoupled state between the two can be measured by supplying a buffer solution (which is a liquid sample containing no specific substance) to the coupled body fixed to the measuring chip. Furthermore, in the case where gas is employed as a sample, or the case where a liquid sample containing gas is employed, the sample can be easily supplied onto the measuring chip by the flow passage mechanism.

Thus, various advantages are obtained by continuously supplying a liquid sample. However, a large quantity of the liquid sample must be prepared to continuously supply the liquid sample onto the measuring chip, or it is difficult to measure a wide variety of samples in a short time. Because of this, a user cannot perform a desirable measurement unless the user uses both a sensor which employs a measuring chip in the shape of a well, and a sensor equipped with a measuring chip in the shape of a flat plate and a flow passage mechanism.

SUMMARY OF THE INVENTION

The present invention has been made in view of the above-described circumstances. Accordingly, it is the primary object of the present invention to provide a sensor, utilizing an evanescent wave, which is capable of performing a normal measurement which is performed with a sample held in the measuring chip, and a measurement which is performed while continuously supplying a sample within the measuring chip.

To achieve this end and in accordance with the present invention, there is provided a sensor utilizing an evanescent wave, comprising a light source for emitting a light beam and a measuring chip formed into the shape of a well. The measuring chip comprises a dielectric block transparent to the light beam, a thin film layer formed on one surface of the dielectric block, and a sample holding mechanism for holding a sample on a surface of the thin film layer. The sensor also comprises an optical system for making the light beam enter the dielectric block at angles of incidence so that a total internal reflection condition is satisfied at an interface between the dielectric block and the thin film layer; photodetection means for detecting the intensity of the light beam totally reflected at the interface; and measurement means for measuring a state of attenuated total reflection, based on the result of detection obtained by the photodetection means. The sensor further comprises sample supply-discharge means which is detachably installed within the measuring chip. The sample supply-discharge means is used for continuously supplying the sample onto the surface of the thin film layer and continuously discharging the supplied sample from the surface of the thin film layer.

In continuously discharging the supplied sample from the surface of the thin film layer, the supplied sample may be discharged by suction, etc. Alternatively, by continuously supplying the sample to a closed space connected with a discharge passage, the sample may be discharged through the discharge passage.

In the sensor of the present invention, the sample supply-discharge means may comprise a supply passage for supplying the sample onto the surface of the thin film layer, a discharge passage for discharging the sample from the surface of the thin film layer, and a passage holder for holding the supply passage and the discharge passage so that the two passages are installed detachably within the measuring chip.

The aforementioned passage holder may have a bottom surface at which an exit of the supply passage and an inlet of the discharge passage are opened, and may also have sealing means which surrounds the exit and the inlet, at a region of the bottom surface which contacts the surface of the thin film layer.

The sensor of the present invention utilizing an evanescent wave has the following advantages:

(1) The sensor is constructed so that it is detachably installed within the measuring chip formed into the shape of a well. In addition, the sensor is equipped with the sample supply-discharge means, which is used for continuously supplying the sample onto the surface of the thin film layer and continuously discharging the supplied sample from the surface of the thin film layer. Therefore, the sensor is capable of performing a normal measurement that is performed with a sample held in the measuring chip, and a measurement that is performed while continuously supplying a sample within the measuring chip.

(2) In the case where a sensing substance is fixed on the thin film layer, and the coupled state between a specific substance in a liquid sample and the sensing substance is measured, a new liquid sample can be continuously supplied. Therefore, the concentration of the target substance in the liquid sample can be kept constant during measurement, and the coupled state can be accurately measured. In addition, the coupling coefficient can be easily measured. Furthermore, by using the above-described sample supply-discharge means, a buffer solution can be supplied continuously to the thin film layer of the measuring chip on which the sensing substance coupled by the specific substance is fixed. Therefore, the decoupled state between the sensing substance and the specific substance can be accurately measured. In addition, the decoupling coefficient, etc., can be easily measured.

(3) The sample supply-discharge means is detachably installed within the measuring chip. Therefore, either a normal measurement which is performed with the liquid sample held within the measuring chip without installing the sample supply-discharge means in the measuring chip, or a measurement which is performed while continuously supplying the liquid sample within the measuring chip 9 by the sample supply-discharge means installed within the measuring chip, can be suitably selected according to the object of measurement.

(4) The sample supply-discharge means comprises a supply passage for supplying the sample onto the surface of the thin film layer, a discharge passage for discharging the sample from the surface of the thin film layer, and a passage holder for holding the supply passage and the discharge passage so that the two passages are installed detachably within the measuring chip. In this case, the sample supply-discharge means can be easily installed detachably within the measuring chip.

(5) The aforementioned passage holder has a bottom surface at which an exit of the supply passage and an inlet of the discharge passage are opened, and also has sealing means which surrounds the exit and the inlet, at a region of the bottom surface which contacts the surface of the thin film layer. Therefore, there is no possibility that the sample will leak out of the sample supply-discharge means. When the sample is changed to a different kind of sample and measurements are continued, a reduction in accuracy of measurement can be prevented.

BRIEF DESCRIPTION OF THE DRAWINGS

The present invention will be described in further detail with reference to the accompanying drawings wherein.

DESCRIPTION OF THE PREFERRED EMBODIMENTS

Figure 1:
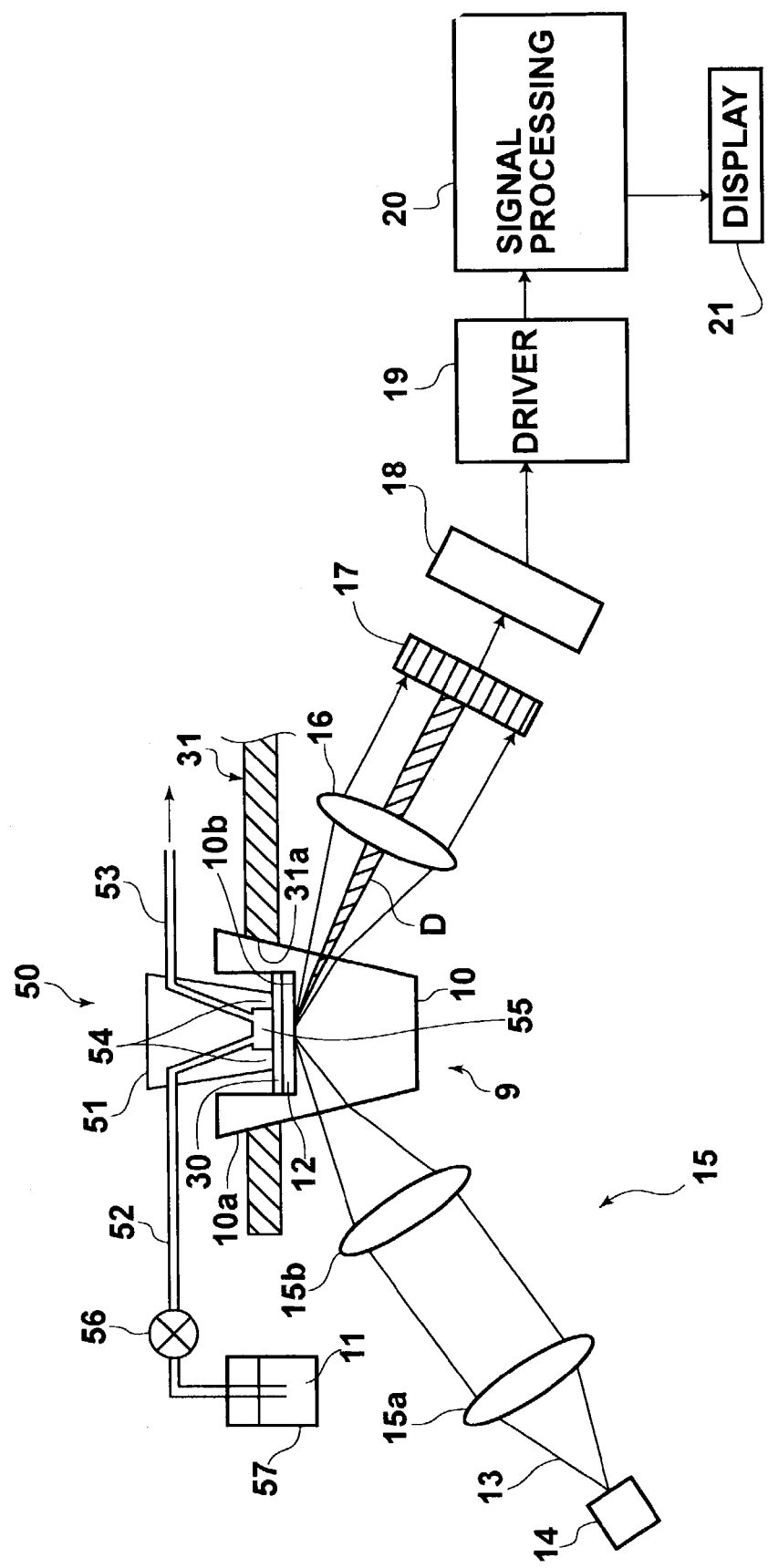
FIG. 1 is a side view showing a surface plasmon resonance sensor constructed in accordance with a first embodiment of the present invention.
Figure 2A:
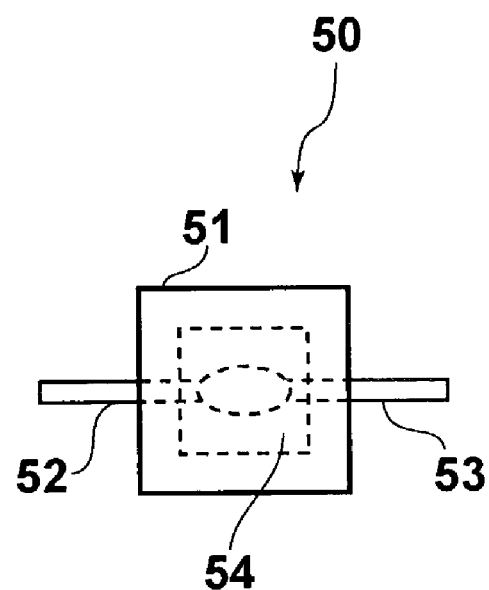
FIG. 2A is a top view showing a flow passage unit employed in the surface plasmon resonance sensor.
Figure 2B:
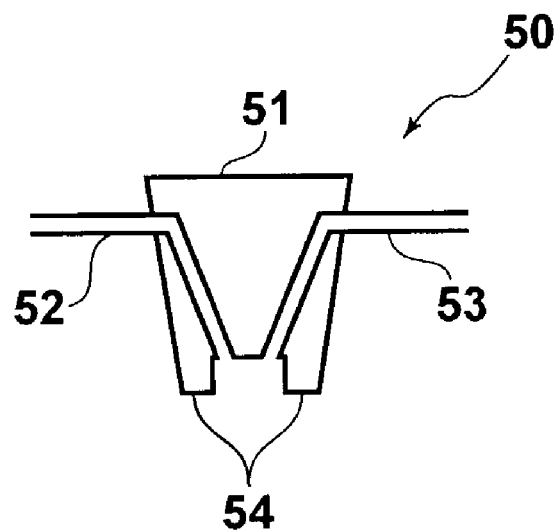
FIG. 2B is a side view showing the flow passage unit.

Referring now in greater detail to the drawings and initially to FIGS. 1 and 2, there is shown a sensor utilizing an evanescent wave, constructed in accordance with a first embodiment of the present invention. The sensor of the first embodiment is a surface plasmon resonance sensor utilizing surface plasmon resonance.

The surface plasmon resonance sensor has a measuring chip 9 formed into the shape of a well, which consists of a dielectric block 10 and a metal film 12. The dielectric block 10 is formed, for example, into the shape of a truncated quadrangular pyramid. The metal film 12 is formed on one surface (e.g., the top surface in FIG. 1) of the dielectric block 10 and made of gold, silver, copper, aluminum, etc.

The dielectric block 10 is formed, for example, from transparent resin, etc., and has a sample holder portion 10a for holding a liquid sample 11 on the metal film 12. In the first embodiment, a sensing substance 30 (which is to be described later) is fixed on the metal film 12.

Within the sample holding portion 10a of the measuring chip 9, there is installed a flow passage unit 50 for forming flow passages over the metal film 12. The flow passage unit 50, as shown in FIG. 2, includes a passage holder 51 formed into the shape of a generally truncated quadrangular pyramid, a supply passage 52 for supplying the liquid sample 11, and a discharge passage 53 for discharging the liquid sample 11. The flow passage unit 50 can be easily installed detachably within the sample holding portion 10a of the measuring chip 9. As shown in FIG. 2, the exit of the supply passage 52 and the inlet of the discharge passage 53 are opened at the bottom surface of the passage holder 51 so that they face the surface of the metal film 12. In addition, the bottom surface of the passage holder 51 which contacts the metal film surface is provided with a sealing portion 54, which surrounds the exit of the supply passage 52 and the inlet of the discharge passage 53. Therefore, when the flow passage unit 50 is placed on the metal film 12 of the measuring chip 9, a sealed passage 55 is formed by the metal film 12 and the sealing portion 54, as shown in FIG. 1. Note that the sealing portion 54 may be formed integrally with the bottom of the passage holder 51 or formed from a separate member that differs in material from the bottom of the passage holder 51. For example, an O-ring may be attached to the bottom surface of the passage holder 51.

The supply passage 52 of the flow passage unit 50 is connected with a pump 56, which is in turn connected to a reservoir 57. The flow passage unit 50, pump 56, and reservoir 57 serve as the sample supply-discharge means of the present invention. The reservoir 57 is used to hold the liquid sample 11 containing a target substance.

In addition to the dielectric block 10, the surface plasmon resonance sensor of the first embodiment includes a laser light source 14, an optical system 15, and a collimator lens 16. The light source 14 consists of a semiconductor laser and emits a single light beam 13. The optical system 15 causes the light beam 13 to enter the dielectric block 10 so that various angles of incidence are obtained with respect to the interface 10b between the dielectric block 10 and the metal film 12. The collimator lens 16 collimates the light beam 13 totally reflected at the interface 10b. The surface plasmon resonance sensor further includes a photodiode array 17, a differential amplifier array 18 connected to the photodiode array 17, a driver 19, a signal processing unit 20, and a display unit 21 connected to the signal processing unit 20. The photodiode array 17 detects the collimated light beam 13. The signal processing unit 20 is constructed of a computer system, etc.

The optical incidence system 15 is constructed of a collimating lens 15a and a light-gathering lens 15b. The collimating lens 15a is used to collimate the light beam 13 emitted divergently from the laser light source 14. The light-gathering lens 15b is used to cause the collimated light beam 13 to converge at the above-described interface 10b. Note that much of the light beam 13 from the laser light source 14 is gathered and directed to the interface 10b within the flow passage area 51 by the light-gathering lens 15b.

The light beam 13 has components that strike the interface 10b at various incidence angles $\theta$, because much of it is gathered as described above. Note that the optical incidence system 15 is constructed so that the incidence angles $\theta$ become greater than a critical angle at which total internal reflection (TIR) occurs. Therefore, the light beam 13 is totally reflected at the interface 10b and includes components reflected at various angles of reflection. Notice that the optical incidence system 15 may be constructed so that the light beam 13 strikes the interface 10b in a defocused state. In this case, errors in the detection of surface plasmon resonance are averaged and accuracy of measurement is enhanced.

The light beam 13 is caused to strike the interface 10b as p-polarized light. Because of this, the laser light source 14 is disposed so that the direction of polarization becomes a predetermined direction. Alternatively, the polarization direction of the light beam 13 may be controlled with a wavelength plate, etc.

Now, a description will be given of how a sample is analyzed by the above-described surface plasmon resonance sensor. Prior to measurements, the above-described measuring chip 9 is fitted in a chip-holding hole 31a formed in a turntable 31. Next, the flow passage unit 50 is installed within the measuring chip 9 so that the sealing portion 54 of the unit 50 is brought into intimate contact with the metal layer 12 of the measuring chip 9. The pump 56 is operated to supply the liquid sample 11 in the reservoir 57 to the sample-measuring passage 55 through the supply passage 52 of the flow passage unit 50. During measurement, the pump 56 is operated so that the liquid sample 11 is supplied continuously to the sample-measuring passage 55. Since the sample-measuring passage 55 is sealed by the sealing portion 54, the liquid sample 11 supplied to the sample-measuring passage 55 is discharged through the discharge passage 53.

After the liquid sample 11 is supplied within the sample-measuring passage 55, the measurement is started. As previously described, the liquid sample 11 is supplied continuously during measurement. As shown in FIG. 1, the light beam 13 from the laser light source 14 is converged on the interface 10b between the dielectric block 10 and the metal film 12 by the optical system 15. Therefore, the light beam 13 includes components incident at various incidence angles $\theta$ with respect to the interface 10b. As previously described, the optical system 15 is constructed so that the incidence angles $\theta$ become greater than a critical angle at which total internal reflection (TIR) occurs. Hence, the light beam 13 is totally reflected at the interface 10b and includes components reflected at various angles of reflection.

The light beam 13 reflected at the interface 10b is collimated by the collimator lens 16 and is detected by the photodiode array 17. The photodiode array 17 in the first embodiment includes a plurality of photodiodes 17a, 17b, 17c, . . . juxtaposed in a row. As shown in FIG. 1, the direction of the juxtaposed photodiodes is approximately perpendicular to the traveling direction of the collimated light beam 13. Therefore, the components of the light beam 13 reflected at various angles at the interface 10b are separately received by the different photodiodes 17a, 17b, 17c, . . .

Figure 3:
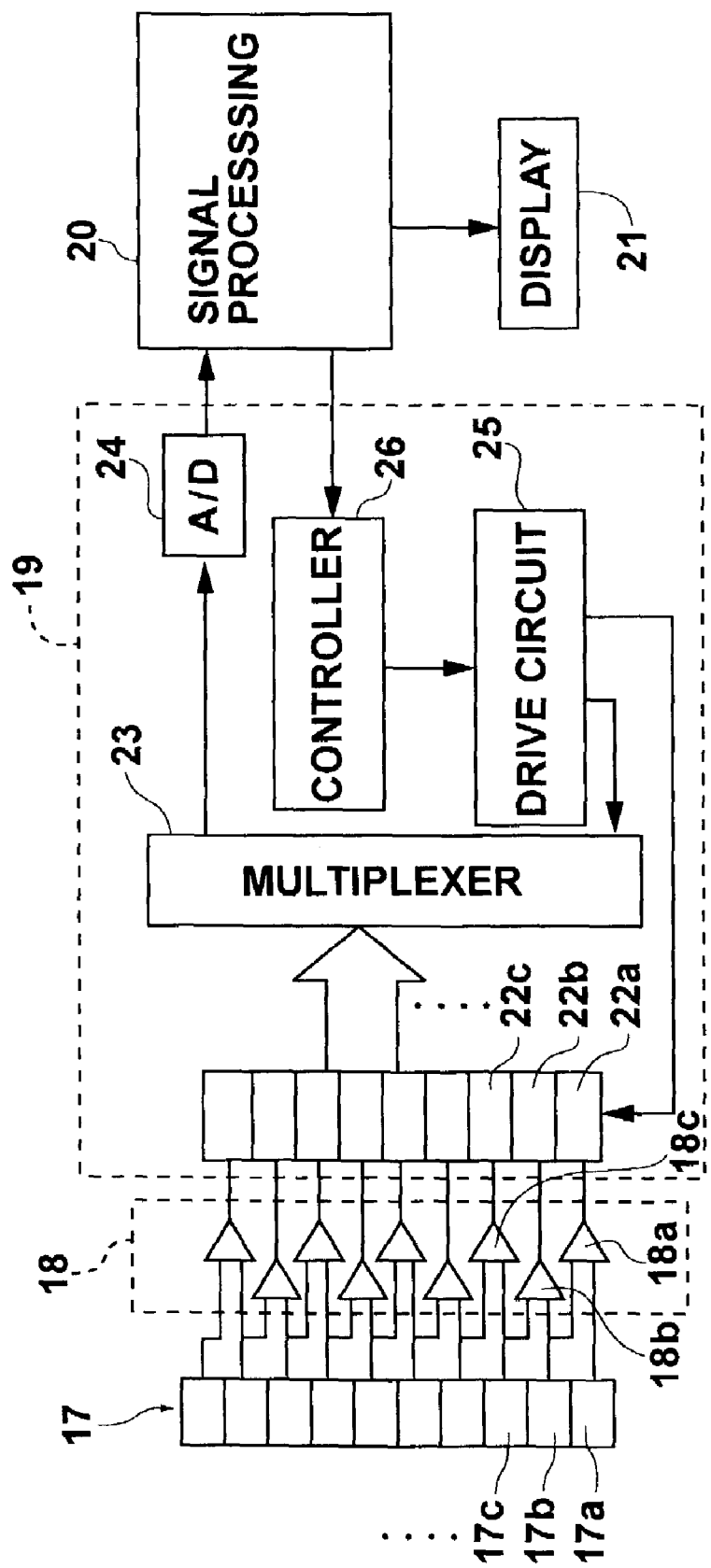
FIG. 3 is a block diagram showing the electrical construction of the surface plasmon resonance sensor.

FIG. 3 shows the electrical construction of the surface plasmon resonance sensor of the first embodiment. As shown in the figure, the driver 19 includes sample-holding circuits 22a, 22b, 22c, . . . , a multiplexer 23, an A/D converter 24, a drive circuit 25, and a controller 26. The sample-holding circuits 22a, 22b, 22c, . . . hold the outputs of the differential amplifiers 18a, 18b, 18c, . . . of the differential amplifier array 18, respectively. The outputs of the sample-holding circuits 22a, 22b, 22c, . . . are input to the multiplexer 23. The A/D converter 24 digitizes the output of the multiplexer 23 and then inputs the digitized output to the signal processing unit 20. The drive circuit 25 drives the multiplexer 23 and the sample-holding circuits 22a, 22b, 22c, . . . . The controller 26 controls operation of the drive circuit 25 in response to a command from the signal processing unit 20.

The outputs of the photodiodes 17a, 17b, 17c, . . . are input to the differential amplifiers 18a, 18b, 18c, . . . of the differential amplifier array 18. Note that the outputs of two adjacent photodiodes are input in common to a single differential amplifier. Therefore, the outputs of the differential amplifiers 18a, 18b, 18c, . . . are considered to be values obtained by differentiating the output signals of the photodiodes 17a, 17b, 17c, . . . in the direction where the photodiodes 17a, 17b, 17c, . . . are juxtaposed.

The outputs of the differential amplifiers 18a, 18b, 18c, . . . are held at predetermined timings by the sample-holding circuits 22a, 22b, 22c, . . . , respectively. The outputs of the sample-holding circuits 22a, 22b, 22c, . . . are input to the multiplexer 23. The multiplexer 23 inputs the held outputs of the differential amplifiers 18a, 18b, 18c, . . . to the A/D converter 24 in a predetermined order. The A/D converter 24 digitizes these outputs and then inputs the digitized signals to the signal processing unit 20.

Figure 4A:
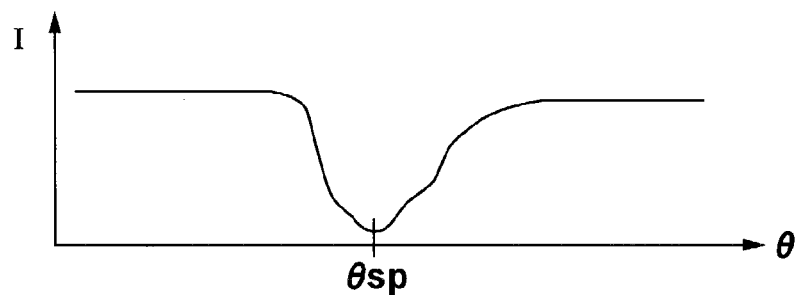
FIG. 4A is a graph showing the relationship between the incidence angle at which a light beam enters the measuring chip of the surface plasmon resonance sensor, and the intensity of the light beam reflected at the measuring chip.

FIG. 4A shows the relationship between the incidence angle θ of the light beam 13 with respect to the interface 10b and the intensity I of the light beam 13 reflected at the interface 10b. Light, incident at a specific angle $\theta_{sp}$ on the interface 10b between the metal film 12 and the liquid sample 11, excites a surface plasmon on the interface 10b. Because of this, the intensity I of the light beam 13 totally reflected at the interface 10b drops sharply. That is, the specific incidence angle $\theta_{sp}$ is an angle at which attenuated total reflection (ATR) occurs. At the attenuated total reflection angle $\theta_{sp}$, the intensity I of the reflected light beam 13 becomes the minimum value. The sharp drop in the intensity I is observed as a dark line in the reflected light, as shown at D in FIG. 1.

Figure 4B:
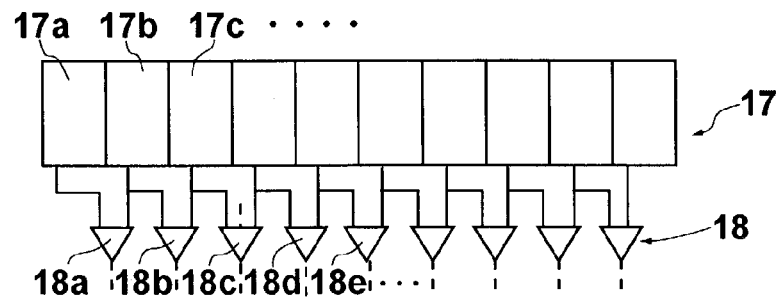
FIG. 4B is a diagram showing a photodiode array employed in the surface plasmon resonance sensor.

FIG. 4B shows the direction in which the photodiodes 17a, 17b, 17c, . . . are juxtaposed with one another. As previously described, the positions of the photodiodes 17a, 17b, 17c, . . . correspond to the above-mentioned incidence angles θ, respectively.

Figure 4C:
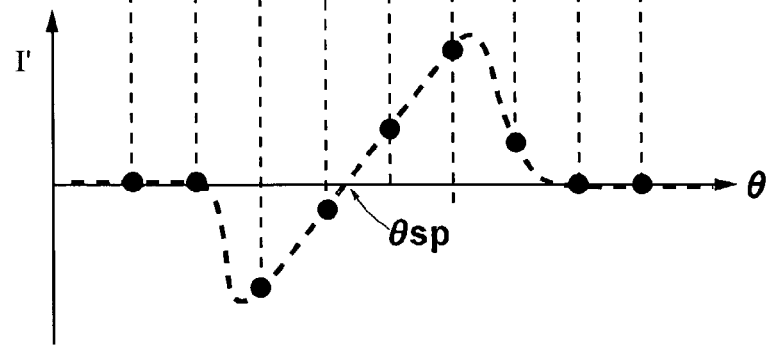
FIG. 4C is a graph showing the relationship between the incidence angle of the light beam and the differentiated value of the output of the photodiode array.

FIG. 4C shows the relationship between the positions of the photodiodes 17a, 17b, 17c, . . . (i.e., the incidence angles θ) and the outputs I' of the differential amplifiers 18a, 18b, 18c, . . . (i.e., differentiated values of the intensities I).

Based on the differentiated value I' input from the A/D converter 24, the signal processing unit 20 selects a differential amplifier (e.g., the differential amplifier 18d in FIG. 3) whose output is closest to a differentiated value of I'=0 corresponding to the attenuated total reflection angle $\theta_{sp}$, from among the differential amplifiers 18a, 18b, 18c, . . . . Then, a differentiated value I' output from the selected differential amplifier undergoes a predetermined correction process, and the corrected value is displayed on the display unit 21. Note that there are cases where a differential amplifier outputting a differentiated value of I'=0 is present. In that case, it is a matter of course that the differential amplifier is selected.

Thereafter, each time a predetermined time elapses, the differentiated value I' output from the selected differential amplifier 18d undergoes a predetermined correction process and is displayed on the display unit 21. If the dielectric constant or refractive index of the sensing substance 30 in contact with the metal film 12 of the measuring chip 9 changes and therefore the curve in FIG. 4A is shifted in the horizontal direction, then the differentiated value I' is increased or decreased according to the horizontal shift. Therefore, by continuously measuring the differentiated value I' with the lapse of time, a change in the refractive index of the sensing substance 30 in contact with the metal film 12 can be detected.

Particularly, in the first embodiment, if a target substance contained in the liquid sample 11 is a specific substance that couples with the sensing substance 30, then the refractive index of the sensing substance 30 changes according to the coupled state between the sensing substance 30 and the target substance. Therefore, by continuously measuring the differentiated value I', it can be detected whether or not a target substance contained in the liquid sample 11 is a specific substance that couples with the sensing substance 30.

In the first embodiment, the supply of the liquid sample 11 to the sample-measuring passage 55 continues until the end of measurement. Therefore, the concentration of the target substance in the liquid sample 11 is kept constant during the time from the start of measurement to the end of measurement.

In addition, in the case where a target substance in the liquid sample 11 is coupled to the sensing substance 30, how the decoupled state between the target substance and the sensing substance 30 changes with the lapse of time can be detected after the measurement of the coupled state. In this case, a buffer solution, which is a liquid sample containing no target substance, is supplied continuously to the sensing substance 30 coupled by the target substance, and the measurement is performed. The target substance being coupled to the sensing substance 30 is decoupled gradually into the buffer solution, and the refractive index of the sensing substance 30 changes according to the decoupled state between the target substance and the sensing substance 30. Therefore, by continuously measuring the differentiated value I', it can be accurately detected how the decoupled state changes. In addition, the decoupling coefficient can be easily found, because a new buffer solution is always supplied.

As evident in the foregoing description, the sensor of the first embodiment utilizing an evanescent wave has the following advantages:

(1) The sensing substance 30 is fixed on the metal film 12. In measuring the coupled state between a target substance in the liquid sample 11 and the sensing substance 30, a new liquid sample 11 can be continuously supplied within the measuring chip 9 through the flow passage unit 50. Therefore, the concentration of the target substance in the liquid sample 11 can be kept constant during measurement. As a result, the coupled state can be accurately measured. In addition, the coupling coefficient, etc., can be easily found. Furthermore, a buffer solution, which is a liquid sample containing no target substance, is supplied continuously to the metal film 12 of the measuring chip 9 on which the sensing substance 30 coupled by the target substance is fixed. Therefore, the decoupled state between the sensing substance 30 and the target substance can be measured with a high degree of accuracy. In addition, the decoupling coefficient, etc., can be easily found.

(2) The flow passage unit 50 is detachably installed within the measuring chip 9. Therefore, either a normal measurement which is performed with the liquid sample 11 held within the measuring chip 9 without installing the flow passage unit 50 in the measuring chip 9, or a measurement which is performed while continuously supplying the liquid sample 11 within the measuring chip 9 by the flow passage holder 51 installed within the measuring chip 9, can be suitably selected according to the object of measurement. The flow passage unit 50 includes the supply passage 52, the discharge passage 53, and the passage holder 51. As a result, the flow passage unit 50 is easily installed detachably within the measuring chip 9.

(3) The passage holder 51 is equipped with the sealing portion 54. Therefore, there is no possibility that the liquid sample 11 will leak out of the measuring passage 55. Even in the case where the decoupled state is measured following the measurement of the coupled state, as described above, there is no possibility that the liquid sample containing a target substance will be mixed with the liquid sample 11 containing no target substance. As a result, a reduction in accuracy of measurement can be prevented.

Note that the first embodiment is not limited to the above-described method of measuring the coupled state between a target substance in the liquid sample 11 and the sensing substance 30. For instance, if a liquid sample containing gas is supplied by the flow passage unit 50 to the measuring chip 9 in which the sensing substance 30 is not fixed, the refractive index of this liquid sample can be accurately measured.

Note that in order to observe how the coupled state between a specific substance in the liquid sample 11 and the sensing substance 30 changes with the lapse of time, the differentiated value I' may be calculated and displayed each time a predetermined time elapses. In addition, between the initial differentiated value I' (0) and the differentiated value I' (t) measured when a predetermined time elapses, the difference ΔI' may be calculated and displayed.

Figure 5A:
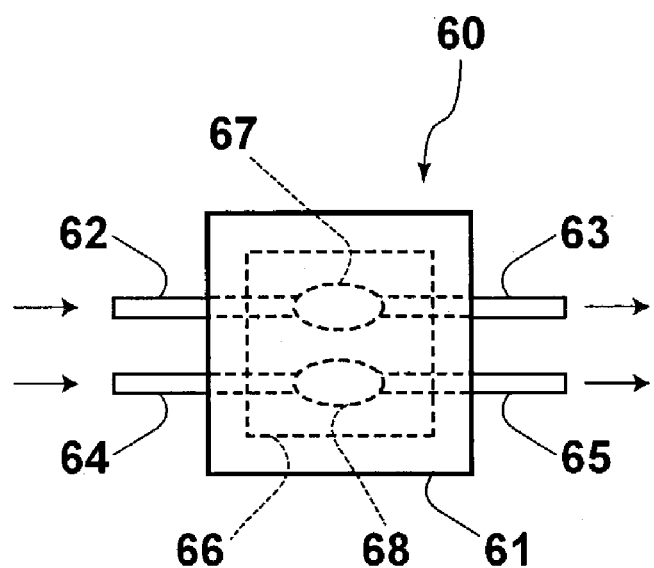
FIG. 5A is a top view showing a first modification of the flow passage unit.

Referring now to FIG. 5A, there is shown a second flow passage unit 60 equipped with a plurality of supply passages and a plurality of discharge passages. That is, the second flow passage unit 60 includes a passage holder 61 formed into the shape of a truncated quadrangular pyramid, a first supply passage 62 and a second supply passage 64 for supplying a liquid sample, and a first discharge passage 63 and a second discharge passage 65 for discharging the liquid sample. The flow passage unit 60 can be easily installed detachably within the measuring chip 9. The exit of the first supply passage 62 and the inlet of the first discharge passage 63 are opened at the bottom surface of the passage holder 61 so that they face the surface of the metal film 12. Similarly, the exit of the second supply passage 64 and the inlet of the second discharge passage 65 are opened at the bottom surface of the passage holder 61 so that they face the surface of the metal film 12. In addition, the bottom surface of the passage holder 61 which contacts the metal film surface is provided with a sealing portion 66, which surrounds the exit of the first supply passage 62, the inlet of the first discharge passage 63, the exit of the second supply passage 64, and the inlet of the second discharge passage 65. Therefore, when the flow passage unit 60 is installed within the measuring chip 9, a first sample-measuring passage 67 and a second sample-measuring passage 68 are formed by the metal film 12 and the sealing portion 66, as shown in FIG. 5A.

Figure 5B:
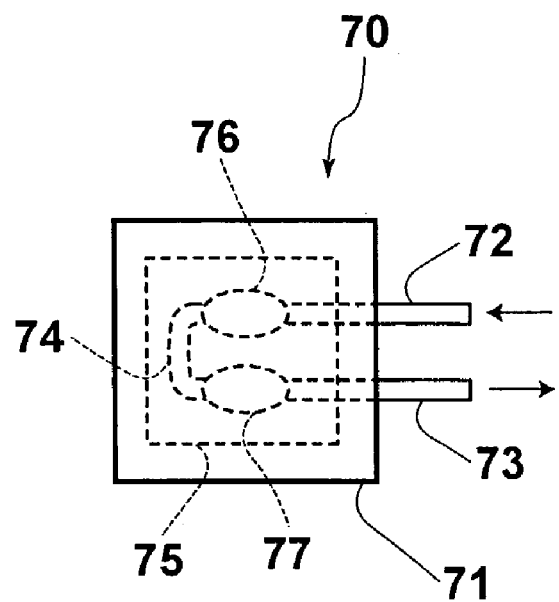
FIG. 5B is a top view showing a second modification of the flow passage unit.

Referring now to FIG. 5B, there is shown a third flow passage unit 70 equipped with a supply passage, a connection passage, and a discharge passage. That is, the third flow passage unit 70 includes a passage holder 71 formed into the shape of a truncated quadrangular pyramid, a supply passage 72 for supplying a liquid sample, a discharge passage 73 for discharging the liquid sample, and a connection passage 74 for connecting passages within the passage holder 71. The flow passage unit 70 can be easily installed detachably within the measuring chip 9. The exit of the supply passage 73 and the inlet of the connection passage 74 are opened at the bottom surface of the passage holder 67 so that they face the surface of the metal film 12. Likewise, the exit of the connection passage 74 and the inlet of discharge passage 73 are opened at the bottom surface of the passage holder 71 so that they face the surface of the metal film 12. In addition, the bottom surface of the passage holder 71 which contacts the metal film surface is provided with a sealing portion 75, which surrounds the exit of the supply passage 72, the inlet of the connection passage 74, the exit of the connection passage 74, and the inlet of the discharge passage 73. Therefore, when the flow passage unit 70 is installed within the measuring chip 9, a first sample-measuring passage 76 and a second sample-measuring passage 77 are formed by the metal film 12 and the sealing portion 75, as shown in FIG. 5B.

In the third flow passage unit 70, a measuring chip may be produced so that the sensing substance 30 is fixed on the half region of the surface of the metal film 12 and that the sensing substance 30 is not fixed on the remaining region. The third flow passage unit 70 is installed within the measuring chip 9 so that the first and second sample-measuring passages 76 and 77 are formed on the respective regions. By finding the difference between values measured from the two passages, measurement errors due to a change in the temperature of a liquid sample can be eliminated.

In the case of the second flow passage unit 60 or third flow passage unit 70, there may be provided two measuring systems consisting of a laser light source 14, an optical system 15, a collimator lens 16, and a photodiode array 17. The two measuring systems maybe employed at the same time, or one of the two measuring systems may be employed. Furthermore, by moving the measuring system or measuring chip 9, measurements may be performed in a time-division manner.

As a modification of the first embodiment, the flow passage unit 50 may be installed within the measuring chip 9 so that the bottom surface of the passage holder 51 is not contacted with the surface of the metal film 12. In such a case, an O-ring, etc., may be provided between the passage holder 51 and the measuring chip 9, or a suction function may be provided on the side of the discharge passage 53 so that the quantity of the liquid sample 11 supplied becomes equal to the quantity of the liquid sample 11 discharged.

Figure 6:
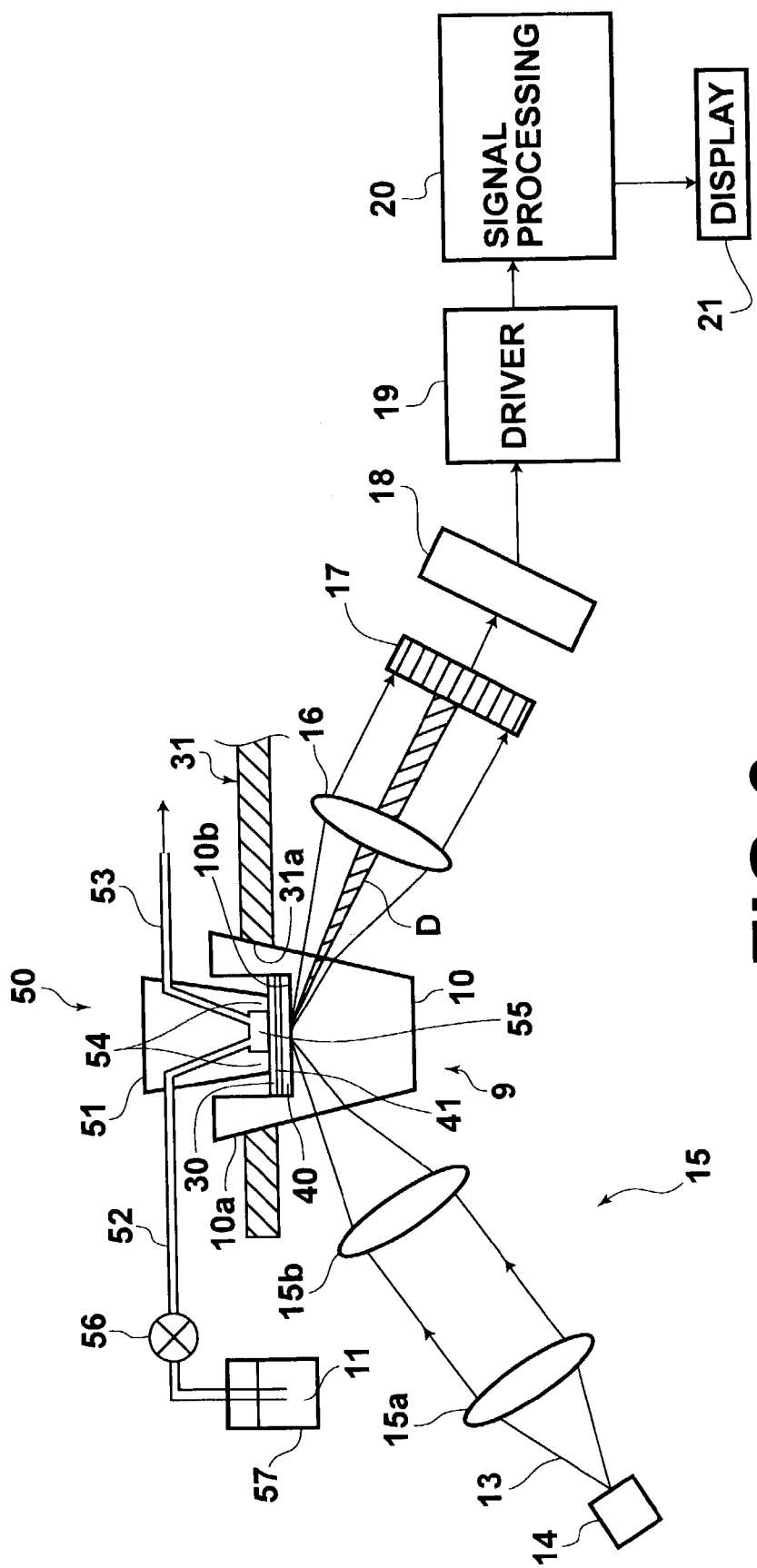
FIG. 6 is a side view showing a leaky mode sensor constructed in accordance with a second embodiment of the present invention.

Referring to FIG. 6, there is shown a sensor constructed in accordance with a second embodiment of the present invention. Since the same reference numerals are applied to the same parts as those of FIG. 1, descriptions thereof are omitted unless particularly necessary.

The sensor of the second embodiment utilizing an evanescent wave is constructed as a leaky mode sensor. As with the first embodiment, the second embodiment is constructed so that it employs a dielectric block 10 as a measuring chip. The dielectric block 10 has a cladding layer 40 formed on one surface thereof (e.g., the top surface in FIG. 6). The cladding layer 40 has an optical waveguide layer 41 formed on the surface thereof.

The dielectric block 10 is formed, for example, from synthetic resin, or optical glass such as BK7, etc. The cladding layer 40 is formed into a thin film from a dielectric lower in refractive index than the dielectric block 10, or metal such as gold, etc. The optical waveguide layer 41 is also formed into a thin film from a dielectric higher in refractive index than the cladding layer 40, such as polymethylmethacrylate (PMMA). The cladding layer 40 is 36.5 nm in thickness in the case where it is formed from a thin gold film. The optical waveguide layer 41 is about 700 nm in thickness in the case where it is formed from PMMA.

In the above-described leaky mode sensor, if a light beam 13 is emitted from a laser light source 14 and strikes the cladding layer 40 through the dielectric block 10 at angles of incidence greater than a critical angle at which total internal reflection (TIR) occurs, then the light beam 13 is totally reflected at the interface 10b between the dielectric block 10 and the cladding layer 40. However, light with a specific wave number, incident on the optical waveguide layer 41 through the cladding layer 40 at a specific angle of incidence, propagates in the optical waveguide layer 41 in a waveguide mode. If the waveguide mode is thus excited, the greater part of the incident light is confined within the optical waveguide layer 41, and consequently, ATR occurs in which the intensity of the light beam 13 totally reflected at the interface 10b drops sharply.

Since the wave number of the light beam 13 propagating in the optical waveguide layer 41 depends on the refractive index of the sensing substance 30 on the optical waveguide layer 41, the refractive index of the sensing substance 30 can be found by finding the attenuated total reflection angle at which ATR occurs. In addition, based on the differentiated value I' output from each differential amplifier of the differential amplifier array 18, it can be detected how the coupled state between a target substance in the liquid sample 11 and the sensing substance 30 changes. In the case where a target substance in the liquid sample 11 is coupled to the sensing substance 30, how the decoupled state between the target substance and the sensing substance 30 changes with the lapse of time can be detected by continuously supplying the liquid sample 11 containing no target substance, after the measurement of the coupled state. In addition, the second embodiment is capable of possessing the same advantages as the first embodiment.

Figure 7:
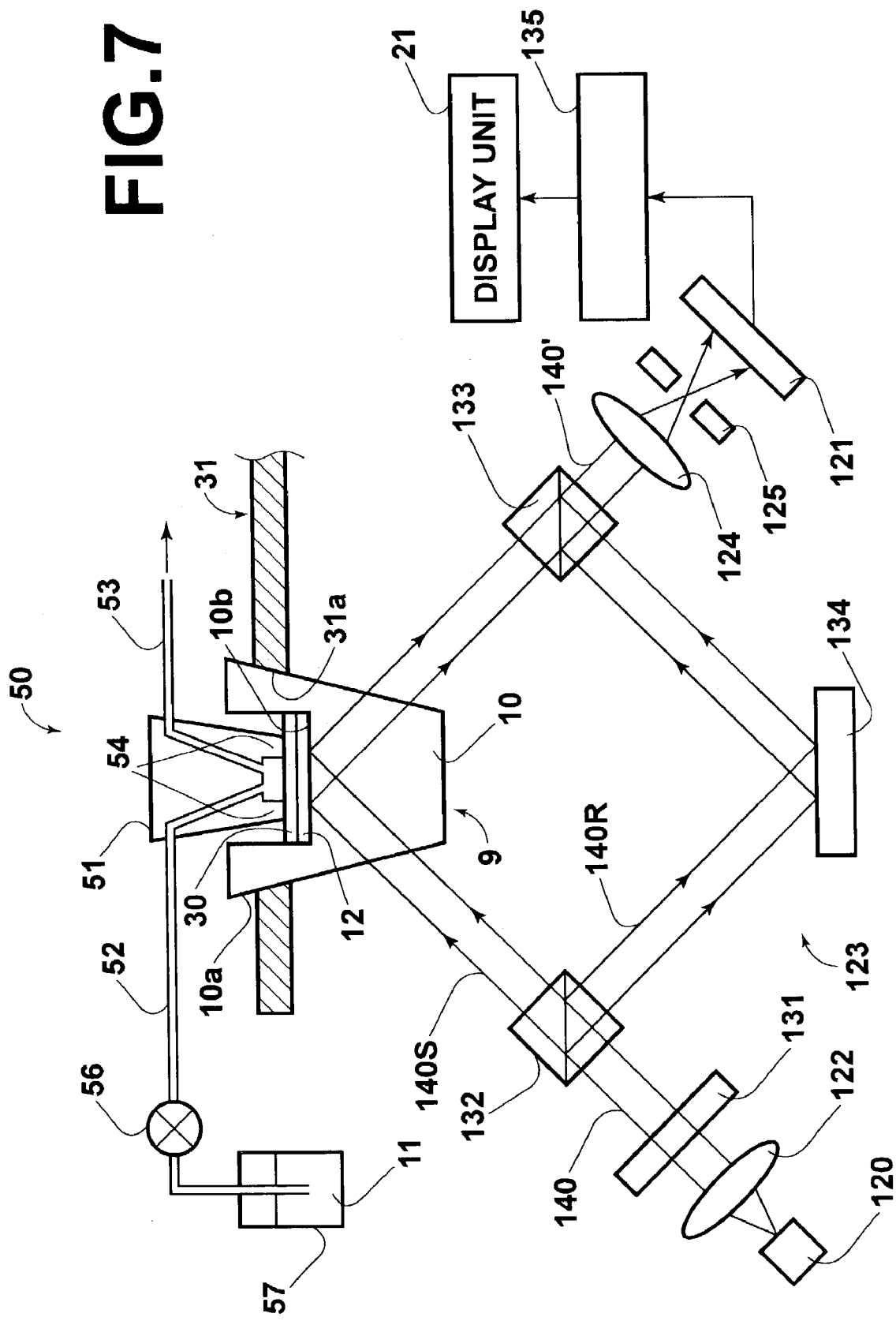
FIG. 7 is a side view showing a surface plasmon resonance sensor constructed in accordance with a third embodiment of the present invention.

Referring to FIG. 7, there is shown a sensor constructed in accordance with a third embodiment of the present invention. Since the same reference numerals are applied to the same parts as those of FIG. 1, descriptions thereof are omitted unless particularly necessary. The sensor of the third embodiment utilizing an evanescent wave is basically the same in construction as the surface plasmon resonance sensor of the first embodiment shown in FIG. 1. However, the method of measurement differs from that of the first embodiment.

As shown in FIG. 7, the surface plasmon resonance sensor of the third embodiment includes a laser light source 120 and a charge-coupled device (CCD) 121, which are disposed at measuring positions. The surface plasmon resonance sensor further includes a collimator lens 122, an optical interference system 123, a condenser lens 124, and an aperture plate 125, which are disposed between the laser light source 120 and the CCD 121.

The optical interference system 123 is constructed of a polarizing filter 131, a first half mirror 132, a second half mirror 133, and a third mirror 134. The CCD 121 is connected to measurement means 135, which is in turn connected to a display unit 21.

A description will hereinafter be given of how measurements are made by the surface plasmon resonance sensor of the third embodiment. The laser light source 121 is driven to emit a light beam 140. The light beam 140 is collimated by the collimator lens 122 and is transmitted through the polarizing filter 131. The light beam 140 from the polarizing filter 131 is split into a first light beam 140S and a second or reference light beam 140R by the first half mirror 132. The first light beam 140S strikes an interface 12a as p-polarized light. The first light beam 140S is totally reflected at the interface 12a, while the second light beam 140R is reflected at the mirror 134. The first light beam 140S and the second light beam 140R are synthesized into a third light beam 140' by the second half mirror 133. Most of the third light beam 140' is gathered by the condenser lens 124. The third light beam 140' is passed through the aperture plate 125 and detected by the CCD 121. The third light beam 140' detected by the CCD 121 produces interference fringes according to the state of the interference between the first light beam 140S and the second light beam 140R.

In the third embodiment, whether a target substance in the liquid sample 11 is coupled to the sensing substance 30 fixed on the surface of the metal film 12 can be judged by measuring the liquid sample 11 continuously after the supply of the liquid sample 11 to the measuring chip 9, and then detecting a change in the interference fringes detected with the CCD 121.

That is, since the refractive index of the sensing substance 30 changes according to the coupled state between the target substance in the liquid sample 11 and the sensing substance 30, the state of interference changes when the first light beam 140S and the second light beam 140R are synthesized by the half mirror 133. Therefore, the coupling reaction can be detected according to a change in the above-described interference fringes. The measurement means 135 detects the coupling reaction, based on the aforementioned principle. The result of detection is displayed on the display unit 21.

As with the first and second embodiments, in the case where a target substance in the liquid sample 11 is coupled to the sensing substance 30, how the decoupled state between the target substance and the sensing substance 30 changes with the lapse of time can be detected by continuously supplying the liquid sample 11 containing no target substance after the measurement of the coupled state. In addition, the third embodiment is capable of possessing the same advantages as the first embodiment.

While the present invention has been described with reference to the preferred embodiments thereof, the invention is not to be limited to the details given herein, but may be modified within the scope of the invention hereinafter claimed.

What is claimed is:

1. A sensor utilizing evanescent wave, comprising:
   a light source for emitting a light beam;
   a measuring chip formed into the shape of a well and comprising
      a dielectric block transparent to said light beam, a thin film layer formed on one surface of said dielectric block, and a sample holding mechanism for holding a sample on a surface of said thin film layer;

an optical system for making said light beam enter said dielectric block at angles of incidence so that a total internal reflection condition is satisfied at an interface between said dielectric block and said thin film layer;

photodetection means for detecting the intensity of said light beam totally reflected at said interface; and measurement means for measuring a state of attenuated total reflection, based on the result of detection obtained by said photodetection means;

wherein said sensor further comprises sample supply-discharge means, which is detachably installed within said measuring chip, for continuously supplying said sample onto the surface of said thin film layer and continuously discharging the supplied sample from the surface of said thin film layer.

2. The sensor as set forth in claim 1, wherein said sample supply-discharge means comprises a supply passage for supplying said sample onto the surface of said thin film layer, a discharge passage for discharging said sample from the surface of said thin film layer, and a passage holder for holding said supply passage and said discharge passage so that the two passages are installed detachably within said measuring chip.

3. The sensor as set forth in claim 1, wherein said sample supply-discharge means comprises a first supply passage for supplying said sample onto a first surface of said thin film layer, a first discharge passage for discharging said sample from said first surface, a second supply passage for supplying said sample onto a second surface of said thin film layer differing from said first surface, a second discharge passage for discharging said sample from said second surface, and a passage holder for holding said first supply passage, said first discharge passage, said second supply passage, and said second discharge passage so that the four passages are installed detachably within said measuring chip.

4. The sensor as set forth in claim 1, wherein said sample supply-discharge means comprises a supply passage for supplying said sample onto a first surface of said thin film layer, a discharge passage for discharging said sample from a second surface of said thin film layer differing from said first surface, a connection passage for connecting said first surface and said second surface, and a passage holder for holding said supply passage, said connection passage, and said discharge passage so that the three passages are installed detachably within said measuring chip.

5. The sensor as set forth in claim 2, wherein said passage holder has a bottom surface at which an exit of said supply passage and an inlet of said discharge passage are opened, and also has sealing means which surrounds said exit and said inlet, at a region of said bottom surface which contacts the surface of said thin film layer.

6. The sensor as set forth in claim 3, wherein said passage holder has a bottom surface at which an exit of said first supply passage, an inlet of said first discharge passage, an exit of said second supply passage, and an inlet of said second discharge passage are opened, and also has sealing means which surrounds the exit of said first supply passage, the inlet of said first discharge passage, the exit of said second supply passage, and the inlet of said second discharge passage, at a region of said bottom surface which contacts the surface of said thin film layer.

7. The sensor as set forth in claim 4, wherein said passage holder has a bottom surface at which an exit of said supply passage, an inlet of said connection passage, an exit of said connection passage, and an inlet of said discharge passage are opened, and also has sealing means which surrounds the exit of said supply passage, the inlet of said connection passage, the exit of said connection passage, and the inlet of said discharge passage, at a region of said bottom surface which contacts the surface of said thin film layer.

8. The sensor according to claim 2, wherein said dielectric block has a recess which accommodates said supply-discharge means.

9. The sensor according to claim 5, wherein said dielectric block has a recess which accommodates said supply-discharge means.

10. The sensor according to claim 2, wherein said passage holder has a recess in a bottom surface of said passage holder and wherein said recess restrainably holds said sample against said thin film layer.

11. The sensor according to claim 5, wherein said passage holder has a recess in the bottom surface of said passage holder and wherein said recess restrainably holds said sample against said thin film layer.

12. The sensor according to claim 3 or 6, wherein said dielectric block has a recess which accommodates said supply-discharge means.

13. The sensor according to claim 6, wherein said dielectric block has a recess which accommodates said supply-discharge means.

14. The sensor according to claim 3, wherein said passage holder has a recess in a bottom surface of said passage holder and wherein said recess restrainably holds said sample against said thin film layer.

15. The sensor according to claim 6, wherein said passage holder has a recess in the bottom surface of said passage holder and wherein said recess restrainably holds said sample against said thin film layer.

16. The sensor according to claim 4, wherein said dielectric block has a recess which accommodates said supply-discharge means.

17. The sensor according to claim 7, wherein said dielectric block has a recess which accommodates said supply-discharge means.

18. The sensor according to claim 4, wherein said passage holder has a recess in a bottom surface of said passage holder and wherein said recess restrainably holds said sample against said thin film layer.

19. The sensor according to claim 4, wherein said passage holder has a recess in the bottom surface of said passage holder and wherein said recess restrainably holds said sample against said thin film layer.

* * * * *